United States Patent
Wang et al.

(10) Patent No.: US 11,753,935 B2
(45) Date of Patent: Sep. 12, 2023

(54) DIRECTIONAL DRILLING-EXPLORING-MONITORING INTEGRATED METHOD FOR GUARANTEEING SAFETY OF UNDERWATER SHIELD TUNNEL

(71) Applicant: China University of Mining and Technology, Jiangsu (CN)

(72) Inventors: Bo Wang, Jiangsu (CN); Xiaozhao Li, Jiangsu (CN); Guanqun Zhou, Jiangsu (CN); Fuqing Li, Jiangsu (CN); Qinghong Dong, Jiangsu (CN); Ziwei Qian, Jiangsu (CN); Siyuan Hu, Jiangsu (CN); Hongyun Chen, Jiangsu (CN)

(73) Assignee: China University of Mining and Technology, Xuzhou (CN)

( * ) Notice: Subject to any disclaimer, the term of this patent is extended or adjusted under 35 U.S.C. 154(b) by 206 days.

(21) Appl. No.: 17/492,956

(22) Filed: Oct. 4, 2021

(65) Prior Publication Data
US 2023/0051333 A1 Feb. 16, 2023

(30) Foreign Application Priority Data
Aug. 11, 2021 (CN) .......................... 202110919140.9

(51) Int. Cl.
*E21D 9/06* (2006.01)
*E21B 7/04* (2006.01)
(Continued)

(52) U.S. Cl.
CPC .............. *E21D 9/003* (2013.01); *E21B 7/046* (2013.01); *E21B 49/003* (2013.01);
(Continued)

(58) Field of Classification Search
CPC . E21D 9/003; E21D 9/06; E21B 7/046; E21B 49/003; E21B 49/005; E21B 2200/20
See application file for complete search history.

(56) References Cited

U.S. PATENT DOCUMENTS

| 11,236,612 B2 * | 2/2022 | Wang | ........................ G01C 7/06 |
| 2020/0018164 A1 * | 1/2020 | Wang | ...................... E21D 9/003 |

FOREIGN PATENT DOCUMENTS

| CN | 205175392 U | * | 4/2016 | ............. E21D 9/003 |
| CN | 108915692 A | * | 11/2018 | |
| CN | 112177624 A | * | 1/2021 | ............. E21D 9/003 |

* cited by examiner

*Primary Examiner* — Frederick L Lagman
(74) *Attorney, Agent, or Firm* — Kirk A. Wilson; Joseph T. Guy; Patent Filing Specialist Inc.

(57) ABSTRACT

A directional drilling-exploring-monitoring integrated method for guaranteeing safety of an underwater shield tunnel includes: drilling a small-diameter borehole below a water area, and establishing an initial geological model; reaming the small-diameter borehole into a large-diameter borehole, placing a parallel electrical method (PEM) power cable and a monitoring optical fiber cable into the large-diameter borehole, acquiring zero field data, primary field data and secondary field data through carbon rod measurement electrodes before tunnel excavation, and processing the data with an existing inversion method to form an inversion image, thereby obtaining a refined geological model of a stratum; starting the tunnel excavation, and respectively acquiring a disturbance condition of rock and soil and a sedimentation and deformation condition of rock and soil around the tunnel during the excavation, thereby implementing safety excavation of the tunnel; and continuously monitoring the tunnel and the surrounding rock and soil in later use of the tunnel.

4 Claims, 1 Drawing Sheet

(51) Int. Cl.
  *E21D 9/00* (2006.01)
  *E21B 49/00* (2006.01)
(52) U.S. Cl.
  CPC .............. *E21B 49/005* (2013.01); *E21D 9/06* (2013.01); *E21B 2200/20* (2020.05)

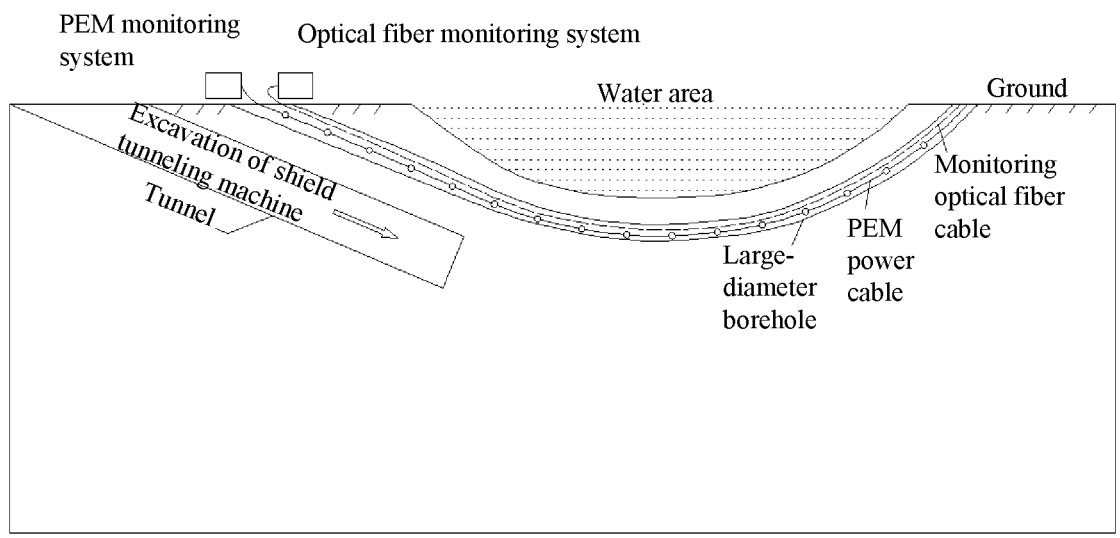

DIRECTIONAL DRILLING-EXPLORING-MONITORING INTEGRATED METHOD FOR GUARANTEEING SAFETY OF UNDERWATER SHIELD TUNNEL

CROSS REFERENCE TO RELATED APPLICATION

This patent application claims the benefit and priority of Chinese Patent Application No. 202110919140.9 filed on Aug. 11, 2021, the disclosure of which is incorporated by reference herein in its entirety as part of the present application.

TECHNICAL FIELD

The present disclosure relates to a method for guaranteeing safety of an underwater shield tunnel, and in particular, to a directional drilling-exploring-monitoring integrated method for guaranteeing safety of an underwater shield tunnel.

BACKGROUND ART

The underground engineering such as tunnel construction below a water area faces great safety risks. For example, in July 2021, due to tunnel excavation below a reservoir, 14 people were dead in the water inrush accident at a 1.16 km location of the Shijingshan Tunnel construction section of the Xingye Express Line (south section) project in Zhuhai, China. Concerning the underground construction such as the tunnel, geological exploration is typically made on a construction area, with an intention of knowing a geological model to guarantee the safety and stability in subsequent exploitation. At present, the ground exploration is mainly used, i.e., an exploration device placed on the ground above the tunnel excavation area performs the geological exploration on the excavation area. This method can effectively implement the geological exploration, but there is often an area unsuitable for the ground exploration operation, which seriously affects the efficiency and safety of the tunnel construction; and particularly for a water area for supplying water to residents or in the natural reserve, the ground exploration for such water area will pollute water, leading to that the ground exploration is unavailable. Hence, how to explore the underwater tunnel and guarantee its construction safety is a problem to be solved.

At present, the commonly used method is advanced exploration which is performed by the exploration device for rock and soil to be excavated in a forward excavating direction below the water area, upon excavating the rock and soil for a certain depth on a side of the water area, so as to obtain the geological model. However, the advanced exploration has the low efficiency as the exploration device is affected by metal of a shield tunneling machine. When a borehole is drilled in front of the shield tunneling machine, the exploration range is small and only the local exploration can be implemented, all of which are difficult to guarantee the safety of the whole tunnel from a larger viewing angle.

In addition, during the tunnel excavation process, the stress of surrounding rock and soil changes to affect the stability. The conventional geophysical exploration method hardly implements continuous monitoring on the rock and soil during the tunnel excavation process and during service of the tunnel upon the completion of the tunnel excavation, let alone the life-cycle continuous monitoring. Therefore, how to effectively explore a geological model below the water area before tunnel excavation to guide the subsequent excavation, and continuously monitor the rock and soil around the tunnel for a long time during and after the tunnel excavation to provide the life-cycle data guidance is a trend to be researched.

SUMMARY

In view of the problems in the prior art, the present disclosure provides a directional drilling-exploring-monitoring integrated method for guaranteeing safety of an underwater shield tunnel. The method can effectively explore a geological model below the water area before tunnel excavation to guide the subsequent excavation, and can further continuously monitor rock and soil around the tunnel for a long time during and after the tunnel excavation to provide life-cycle data guidance.

To achieve the above objective, the present disclosure uses the following technical solutions: a directional drilling-exploring-monitoring integrated method for guaranteeing safety of an underwater shield tunnel specifically includes:

drilling step configured for: drilling a small-diameter borehole at a side of a water area in a directional drilling manner, the small-diameter borehole extending into rock and soil below the water area and extending out of ground at an other side of the water area, thereby completing the drilling of the small-diameter borehole, and the small-diameter borehole having a diameter of 90-108 mm; and recording rock fragments returned from the drilling and a drilling speed in a whole process of the drilling, to comprehensively catalog and analyze information of a stratum through which the small-diameter borehole penetrates, and establish an initial geological model;

reaming step configured for: reaming the small-diameter borehole with a large-diameter drill bit, and performing a slurry supporting during the reaming to form a large-diameter borehole, where the large-diameter borehole has a diameter of 300-400 mm;

stretching step configured for: stretching an end of a parallel-electrical-method (PEM) power cable and an end of a monitoring optical fiber cable into an end of the large-diameter borehole and out of an other end of the large-diameter borehole, where the end of the PEM power cable and the end of the monitoring optical fiber cable are respectively connected to a PEM monitoring system and an optical fiber monitoring system which acquire signals, and n sets of dual-mode electrodes are embedded in the PEM power cable, n=4*(a length of the large-diameter borehole/a height of the tunnel), each set of dual-mode electrodes includes one power supply electrode and one carbon rod measurement electrode, and the one power supply electrode and the one measurement electrode are spaced at 0.2 m;

inspecting step configured for: inspecting a PEM and a signal of an optical fiber, repeating the stretching step in case of no current in the PEM and no communication signal in the optical fiber till an inspection effect is normal, injecting a grouting material having a pressure of 1.5 Mpa into the large-diameter borehole to seal the large-diameter borehole in a whole length of the large-diameter borehole, thereby coupling the power cable, the optical fiber cable and the stratum;

measuring step configured for: measuring, by the PEM monitoring system, zero field data of n carbon rod measurement electrodes; supplying, by the PEM monitoring system, power to n power supply electrodes on the PEM power cable and synchronously measuring primary field data of the n carbon rod measurement electrodes; measuring, by the PEM monitoring system, secondary field data of the n carbon rod measurement electrodes upon completing the supplying of the power; performing multi-parameter non-linear inversion on the zero field data, the primary field data and the secondary field data with an inversion method based on a combination of a back propagation (BP) neural network algorithm and a quantum particle swarm optimization algorithm, to form an inversion image; and updating the initial geological model formed in the drilling step to obtain a refined geological model of the stratum; and determining, according to the refined geological model of the stratum, whether a channel communicating with the water area exists in the stratum to be excavated for the tunnel (the tunnel extending into the stratum from the side of the water area and out of the stratum from the other side of the water area); and taking a measure on the ground if the channel exists;

excavating step configured for: excavating the tunnel below the water area from the side of the water area by means of a shield tunneling machine according to the refined geological model obtained in the measuring step, wherein during a tunnel excavation process, the n sets of dual-mode electrodes of the PEM power cable feed detection data back to the PEM monitoring system in real time, and the PEM monitoring system analyzes and inverts acquired data and compares the acquired data with the inversion image in the measuring step to obtain a disturbance condition of the rock and soil during the excavating; and the optical fiber monitoring system acquires stress, temperature and vibration parameters on the optical fiber in real time to obtain a sedimentation and deformation condition of the rock and soil around the tunnel during the tunnel excavation process;

optimizing step configured for: optimizing a tunnel excavation route in real time according to a real-time monitoring result in the excavating step; performing a reinforcement operation by grouting if a damage of the rock and soil due to the disturbance is monitored during the tunnel excavation process; and monitoring and evaluating a grouting reinforcement effect at a position reinforced by the grouting through the excavating step; and proceeding the excavating after a reinforcement requirement is met; and monitoring step configured for: continuously monitoring, by the PEM power cable and the monitoring optical fiber cable, the tunnel and the rock and soil around the tunnel with a method in the excavating step in later use of the tunnel, after the excavating of the tunnel at the side, below and at the other side of the water area is completed and the tunnel is supported, such that a sedimentation and deformation condition is found timely and handled by a worker subsequently, thereby implementing geological exploration before the tunnel excavation process, real-time disturbance monitoring during the tunnel excavation process and continuous monitoring for the sedimentation and deformation condition after the tunnel excavation process, and guaranteeing life-cycle safety of the tunnel.

Further, the large-diameter borehole is located within 3-5 m above a top of the tunnel. In this way, not only can the continuous monitoring precision of the PEM power cable and the monitoring optical fiber to the underground tunnel be ensured, but also the damage of the PEM power cable and the monitoring optical fiber due to deformation during the tunnel excavation can be reduced.

Further, the n sets of dual-mode electrodes are embedded in the PEM power cable at different distribution densities, where a distribution density of dual-mode electrodes in the PEM power cable below the water area is greater than that of dual-mode electrodes in the PEM power cable on two sides of the water area. With the larger distribution density below the water area, the monitoring precision for the part below the water area is effectively ensured; and the distribution density of the electrodes is reduced as the high precision for the two sides of the water area is not necessary, thereby saving the distribution cost.

Further, the PEM power cable and the monitoring optical fiber cable are bundled together, and installed by drawing the PEM power cable, the PEM power cable has a tensile strength of not less than 3-5 times of a weight thereof, and the PEM power cable has a low loss of signal and a resistance of less than 250 $\Omega$/km. The PEM power cable with such parameters can effectively ensure the stable operation of the PEM power cable during installation and use.

Compared with the prior art, the present disclosure directionally drills, from one side of a water area, a small-diameter borehole that extends into a part below the water area and out of the other side of the water area, and establishes an initial geological model according to acquired information during drilling; reams the small-diameter borehole into a large-diameter borehole, places a PEM power cable and a monitoring optical fiber cable into the large-diameter borehole for installation and detection, acquires zero field data, primary field data and secondary field data through carbon rod measurement electrodes before tunnel excavation, and carries out multi-parameter non-linear inversion on the data with an inversion method based on a combination of a BP neural network algorithm and a quantum particle swarm optimization algorithm to form an inversion image, thereby obtaining a refined geological model of a stratum; starts the tunnel excavation according to the refined geological model, and carries out inversion imaging in real time with the PEM power cable during the excavation to obtain a disturbance condition of rock and soil during the excavation; acquires a sedimentation and deformation condition of rock and soil around the tunnel during the excavation through the monitoring optical fiber cable to implement safety excavation of the tunnel; and continuously monitors the tunnel and the surrounding rock and soil with the PEM power cable and the monitoring optical fiber cable in service of the tunnel, such that the sedimentation and deformation condition can be found timely and handled by a worker subsequently, thereby implementing geological exploration before the tunnel excavation, real-time disturbance monitoring during the excavation and continuous monitoring for the sedimentation and deformation after the excavation, and guaranteeing the life-cycle safety of the tunnel.

BRIEF DESCRIPTION OF THE DRAWINGS

FIG. 1 is a schematic diagram of overall arrangement according to the present disclosure.

DETAILED DESCRIPTION OF THE EMBODIMENTS

The present disclosure is further described below.

As shown in FIG. 1, the method of the present disclosure specifically includes the following steps.

Step 1: A small-diameter borehole is drilled on one side of a water area through a directional drilling method. The small-diameter borehole extends into rock and soil below the water area and extends out of the ground on the other side of the water area, thereby completing drilling of the small-diameter borehole. The small-diameter borehole has a diameter of 90-108 mm Rock fragments returned from the drilling and a drilling speed are recorded in a whole drilling process, to comprehensively catalog and analyze information of a stratum into which the small-diameter borehole penetrates, and establish an initial geological model.

Step 2: The small-diameter borehole is reamed with a large-diameter drill bit, and a slurry wall protection operation is carried out during reaming, finally a large-diameter borehole is formed. The large-diameter borehole has a diameter of 300-400 mm; and the large-diameter borehole is located within 3-5 m from a top of the tunnel to be drilled. In this way, not only can the continuous monitoring precision of the parallel electric method (PEM) power cable and the monitoring optical fiber cable to the underground tunnel be ensured, but also the damage of the PEM power cable and the monitoring optical fiber cable due to deformation during the tunnel excavation can be reduced.

Step 3: One end of the PEM power cable and one end of the monitoring optical fiber cable are stretched into one end of the large-diameter borehole and out of the other end of the large-diameter borehole. One end of the PEM power cable and one end of the monitoring optical fiber cable are respectively connected to a PEM monitoring system and an optical fiber monitoring system which acquire signals. The PEM power cable and the monitoring optical fiber cable are bundled together, and installed by drawing the PEM power cable. The PEM power cable has a tensile strength of not less than 3-5 times of a weight thereof, and the PEM power cable has a low loss of signal and a resistance of less than 250 Ω/km. The PEM power cable with such parameters can effectively ensure the stable operation of the PEM power cable during installation and use. N sets of dual-mode electrodes are embedded on the PEM power cable, n=4*(a length of the borehole/a height of the tunnel), each set of dual-mode electrode includes one power supply electrode and one carbon rod measurement electrode, and the power supply electrode and the measurement electrode are spaced by 0.2 m; both the PEM monitoring system and the optical fiber monitoring system are existing devices. The n sets of dual-mode electrodes are embedded at different distribution densities on the PEM power cable, where a distribution density of dual-mode electrodes on the PEM power cable below the water area is greater than that of dual-mode electrodes on the PEM power cable on two sides of the water area. With the larger distribution density of the dual-mode electrodes below the water area, the monitoring precision for a part below the water area is effectively ensured; as it is no necessary to provide the high precision for the two sides of the water area, the distribution density of the electrodes is reduced, thereby saving the distribution cost.

Step 4: A PEM and a signal of an optical fiber are inspected, Step 3 is repeated in case of no current in the PEM and no communication signal in the optical fiber until an inspection effect is normal, then a grouting material having a pressure of 1.5 Mpa is injected into the large-diameter borehole, and the whole borehole is filled and sealed with the grouting material, thereby coupling the power cable, the optical fiber cable and the stratum.

Step 5: Zero field data of n carbon rod measurement electrodes is measured by the PEM monitoring system; the PEM monitoring system supplies power to n power supply electrodes on the PEM power cable and synchronously measures primary field data of the n carbon rod measurement electrodes. The PEM monitoring system measures secondary field data of the n carbon rod measurement electrodes upon completing the supplying of power. Multi-parameter non-linear inversion is performed on the zero field data, the primary field data and the secondary field data with an inversion method based on a combination of a BP neural network algorithm and a Quantum Particle Swarm Optimization (QPSO) algorithm, to form an inversion image, and update the initial geological model formed in Step 1 to obtain a refined geological model of the stratum; and according to the refined geological model of the stratum, whether a water area conducting channel is present in a stratum to be excavated for the tunnel (the tunnel is excavated from one side of the water area to the other side of the water area) is found, and a measure on the ground is taken if a water area conducting channel is found.

Step 6: The tunnel is excavated below the water area from one side of the water area with a shield tunneling machine according to the refined geological model obtained in Step 5. During the tunnel excavation process, the n sets of dual-mode electrodes of the PEM power cable feed detection data back to the PEM monitoring system in real time. The PEM monitoring system analyzes and inverts acquired data and compares the acquired data with the inversion image in Step 5 to obtain a disturbance condition of the rock and soil during the tunnel excavation process; and the optical fiber monitoring system acquires stress, temperature and vibration parameters on the optical fiber in real time to obtain a sedimentation and deformation condition of rock and soil around the tunnel during the excavation.

Step 7: A tunnel excavation route is optimized in real time according to a real-time monitoring result in Step 6. If a damage of the rock and soil due to the disturbance is monitored during the excavation process, a reinforcement operation is performed by grouting, and a grouting reinforcement effect of a position reinforced by grouting is monitored and evaluated through Step 6; and the excavation work is continued after a reinforcement requirement is met.

Step 8: The PEM power cable and the monitoring optical fiber cable continuously monitor the tunnel and the surrounding rock and soil with a method in Step 6 in later use of the tunnel after the tunnel on one side, below and on the other side of the water area is excavated and supported, such that a sedimentation and deformation condition is found timely and handled by a worker subsequently, thereby implementing geological exploration before the tunnel excavation, real-time disturbance monitoring during the tunnel excavation and continuous monitoring for the sedimentation and deformation after the tunnel excavation, and guaranteeing life-cycle safety of the tunnel.

The foregoing descriptions are only preferred implementations of the present disclosure. It should be noted that several improvements and modifications may further be made by a person of ordinary skill in the art without departing from the principle of the present disclosure, and such improvements and modifications should also be deemed as falling within the protection scope of the present disclosure.

What is claimed is:

1. A directional drilling-exploring-monitoring integrated method for guaranteeing safety of an underwater shield tunnel, comprising:
   drilling step configured for: drilling a small-diameter borehole at a side of a water area in a directional drilling manner, wherein the small-diameter borehole extending into rock and soil below the water area and extending out of ground at an other side of the water area, thereby completing the drilling of the small-diameter borehole, and the small-diameter borehole having a diameter of 90-108 mm; and recording rock fragments returned from the drilling and a drilling speed in a whole process of the drilling, to comprehensively catalog and analyze information of a stratum through which the small-diameter borehole penetrates, and establish an initial geological model;

reaming step configured for: reaming the small-diameter borehole with a large-diameter drill bit, and performing a slurry supporting during the reaming to form a large-diameter borehole, wherein the large-diameter borehole has a diameter of 300-400 mm;

stretching step configured for: stretching an end of a parallel-electrical-method (PEM) power cable and an end of a monitoring optical fiber cable into an end of the large-diameter borehole and out of an other end of the large-diameter borehole, wherein the end of the PEM power cable and the end of the monitoring optical fiber cable are respectively connected to a PEM monitoring system and an optical fiber monitoring system which acquire signals, and n sets of dual-mode electrodes are embedded in the PEM power cable, n=4*(a length of the large-diameter borehole/a height of the tunnel), each set of dual-mode electrodes comprises one power supply electrode and one carbon rod measurement electrode, and the one power supply electrode and the one measurement electrode are spaced at 0.2 m;

inspecting step configured for: inspecting a PEM and a signal of an optical fiber, repeating the stretching step in case of no current in the PEM and no communication signal in the optical fiber till an inspection effect is normal, injecting a grouting material having a pressure of 1.5 Mpa into the large-diameter borehole to seal the large-diameter borehole in a whole length of the large-diameter borehole, thereby coupling the power cable, the optical fiber cable and the stratum;

measuring step configured for: measuring, by the PEM monitoring system, zero field data of n carbon rod measurement electrodes; supplying, by the PEM monitoring system, power to n power supply electrodes on the PEM power cable and synchronously measuring primary field data of the n carbon rod measurement electrodes; measuring, by the PEM monitoring system, secondary field data of the n carbon rod measurement electrodes upon completing the supplying of the power; performing multi-parameter non-linear inversion on the zero field data, the primary field data and the secondary field data with an inversion method based on a combination of a back-propagation neural network algorithm and a quantum particle swarm optimization algorithm, to form an inversion image; and updating the initial geological model formed in the drilling step to obtain a refined geological model of the stratum; and determining, according to the refined geological model of the stratum, whether a channel communicating with the water area exists in the stratum to be excavated for the tunnel; and taking a measure on the ground if the channel exists;

excavating step configured for: excavating the tunnel below the water area from the side of the water area by means of a shield tunneling machine according to the refined geological model obtained in the measuring step, wherein during a tunnel excavation process, the n sets of dual-mode electrodes of the PEM power cable feed detection data back to the PEM monitoring system in real time, and the PEM monitoring system analyzes and inverts acquired data and compares the acquired data with the inversion image in the measuring step to obtain a disturbance condition of the rock and soil during the excavating; and the optical fiber monitoring system acquires stress, temperature and vibration parameters on the optical fiber in real time to obtain a sedimentation and deformation condition of the rock and soil around the tunnel during the tunnel excavation process;

optimizing step configured for: optimizing a tunnel excavation route in real time according to a real-time monitoring result in the excavating step; performing a reinforcement operation by grouting if a damage of the rock and soil due to the disturbance is monitored during the tunnel excavation process; and monitoring and evaluating a grouting reinforcement effect at a position reinforced by the grouting through the excavating step; and proceeding the excavating after a reinforcement requirement is met; and monitoring step configured for: continuously monitoring, by the PEM power cable and the monitoring optical fiber cable, the tunnel and the rock and soil around the tunnel with a method in the excavating step in later use of the tunnel, after the excavating of the tunnel at the side, below and at the other side of the water area is completed and the tunnel is supported, such that a sedimentation and deformation condition is found timely and handled by a worker subsequently, thereby implementing geological exploration before the tunnel excavation process, real-time disturbance monitoring during the tunnel excavation process and continuous monitoring for the sedimentation and deformation condition after the tunnel excavation process, and guaranteeing life-cycle safety of the tunnel.

2. The directional drilling-exploring-monitoring integrated method for guaranteeing safety of the underwater shield tunnel according to claim 1, wherein the large-diameter borehole is located within 3-5 m above a top of the tunnel.

3. The directional drilling-exploring-monitoring integrated method for guaranteeing safety of the underwater shield tunnel according to claim 1, wherein the n sets of dual-mode electrodes are embedded in the PEM power cable at different distribution densities, wherein a distribution density of dual-mode electrodes in the PEM power cable below the water area is greater than that of dual-mode electrodes in the PEM power cable on two sides of the water area.

4. The directional drilling-exploring-monitoring integrated method for guaranteeing safety of the underwater shield tunnel according to claim 1, wherein the PEM power cable and the monitoring optical fiber cable are bundled together, and installed by drawing the PEM power cable, the PEM power cable has a tensile strength of not less than 3-5 times of a weight thereof, and the PEM power cable has a low loss of signal and a resistance of less than 250 $\Omega$/km.

* * * * *